(12) United States Patent
Kuperman

(10) Patent No.: US 8,070,486 B2
(45) Date of Patent: Dec. 6, 2011

(54) METHOD AND APPARATUS FOR INDIRECT BONDING OF ORTHODONTIC APPLIANCES TO TEETH

(76) Inventor: Lester Kuperman, Fort Worth, TX (US)

( * ) Notice: Subject to any disclaimer, the term of this patent is extended or adjusted under 35 U.S.C. 154(b) by 1047 days.

(21) Appl. No.: 10/836,375

(22) Filed: Apr. 30, 2004

(65) Prior Publication Data

US 2005/0244790 A1    Nov. 3, 2005

(51) Int. Cl.
*A61C 3/00* (2006.01)
(52) U.S. Cl. .......................................... 433/24
(58) Field of Classification Search ............... 433/2, 24, 433/213
See application file for complete search history.

(56) References Cited

U.S. PATENT DOCUMENTS

| | | | |
|---|---|---|---|
| 3,949,478 A * | 4/1976 | Schinhammer | 433/3 |
| 4,068,379 A * | 1/1978 | Miller et al. | 433/9 |
| 4,284,405 A * | 8/1981 | Dellinger | 433/24 |
| 4,431,409 A * | 2/1984 | Picard | 433/2 |
| 4,657,508 A | 4/1987 | Dellinger | |
| RE35,169 E | 3/1996 | Lemchen et al. | |
| 5,931,667 A | 8/1999 | Papandreas | |
| 6,123,544 A * | 9/2000 | Cleary | 433/24 |
| 6,250,918 B1 | 6/2001 | Sachdeva et al. | |
| 6,554,613 B1 * | 4/2003 | Sachdeva et al. | 433/24 |
| 6,688,885 B1 | 2/2004 | Sachdeva et al. | |
| 6,699,037 B2 | 3/2004 | Chishti et al. | |
| 7,077,646 B2 * | 7/2006 | Hilliard | 433/6 |
| 2003/0096209 A1 | 5/2003 | Sugiyama et al. | |
| 2003/0194677 A1 | 10/2003 | Sachdeva et al. | |
| 2003/0198911 A1 | 10/2003 | Knopp et al. | |
| 2003/0224316 A1 | 12/2003 | Marshall | |
| 2004/0253562 A1 * | 12/2004 | Knopp | 433/24 |
| 2006/0257821 A1 * | 11/2006 | Cinader et al. | 433/213 |

* cited by examiner

*Primary Examiner* — Ralph Lewis

(74) *Attorney, Agent, or Firm* — Caesar Rivise Bernstein Cohen & Pokotilow, Ltd.

(57) ABSTRACT

A method of indirect bonding and a physical model that allows for optimal positional alignment of orthodontic appliances on a patient's teeth is disclosed. The physical model of the patient's teeth has pods and ridges on the facial surface of the teeth. Adhesive is applied to an orthodontic appliance and the appliance is placed on a tooth of the physical model against the ridge and on top of the pods. The adhesive fills the space in between the appliance and the facial surface of the tooth and adheres to the model, resulting in a dimensionally correct custom base that is properly aligned with the tooth to account for all five positional elements of a tooth. Once all the orthodontic appliances are applied to the model, the appliances can then be removed from the model and bonded to the patient's teeth in the optimal position using a transfer template.

15 Claims, 4 Drawing Sheets

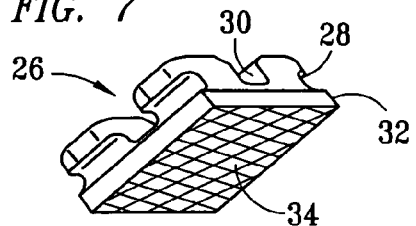
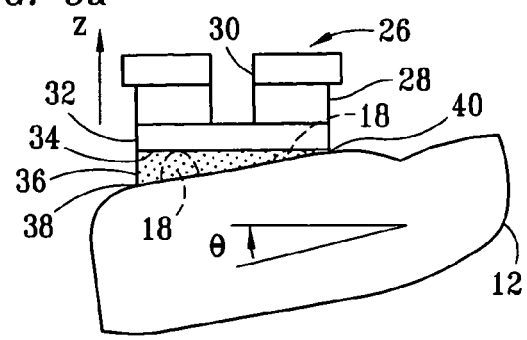
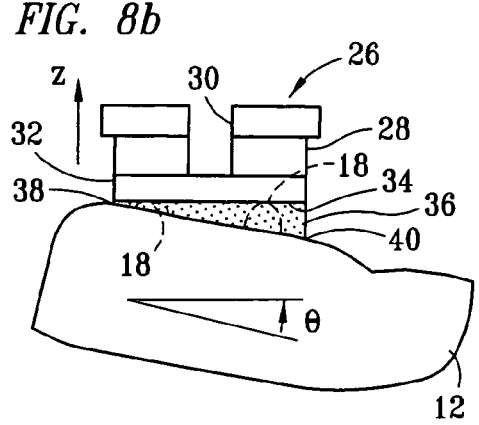
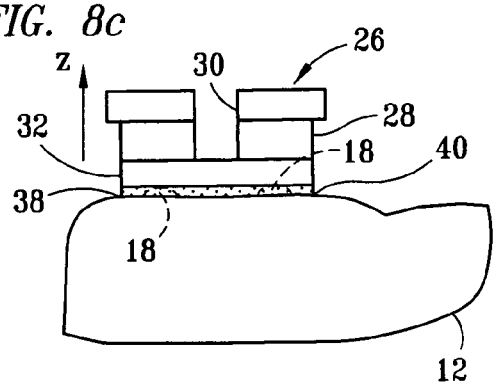
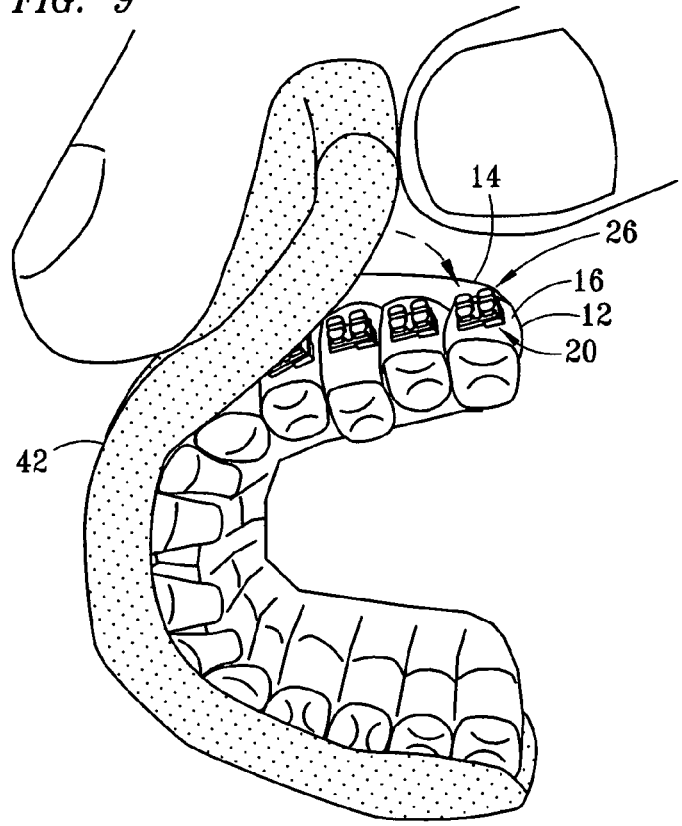

METHOD AND APPARATUS FOR INDIRECT BONDING OF ORTHODONTIC APPLIANCES TO TEETH

BACKGROUND OF THE INVENTION

1. Field of the Invention

This invention relates to the field of orthodontics and, more particularly, to the fabrication of a physical model that serves as a guide for the proper placement of orthodontic appliances, especially brackets, on a patient's teeth when utilizing any of several indirect bonding techniques.

2. Description of Related Art

Orthodontics involves repositioning the teeth to correct a malocclusion. This repositioning can be accomplished using various forms of orthodontic appliances or apparatuses. Fixed orthodontic treatment generally involves the bonding or cementation of bands, brackets, and tubes (collectively "braces") to the teeth. The brackets and tubes serve as "handles" by which gentle forces can be applied to the teeth. Archwires are placed into the bracket slots to achieve the basic alignment direction and forces. Various combinations of elastomeric, elastic, coil spring, and other devices can be used to provide additional, specific forces to the teeth. Proper placement of the brackets on a patient's teeth is one of the most significant determinants of effective tooth movement to the desired location.

The most common form of "braces" is brackets that are bonded to the surface of the teeth. Two techniques for placing brackets on a patient's teeth are direct bonding and indirect bonding. Direct bonding is an intraoral procedure in which orthodontic appliances are oriented by inspection and bonded individually to the tooth surface by the doctor or auxiliary personnel. Indirect bonding is basically a two-step process by which brackets are affixed temporarily to the teeth of a physical model for that specific patient and then transferred all together to the mouth by means of a molded matrix or transfer tray that captures their predetermined orientation and permits them to be bonded simultaneously.

Advantages of indirect bonding compared to direct bonding include more accurate bracket placement, improved access, simultaneous bonding of all brackets, shorter bonding appointment times, and less re-positioning of the brackets due to placement errors. Ideal bracket positioning is the goal that should reduce adjustments to the archwires. All of these advantages result in decreased chair time, decreased orthodontist time, less treatment time, and less patient discomfort.

However, orthodontists are still dissatisfied with available direct and indirect bonding because existing techniques do not allow the orthodontist to optimally position orthodontic appliances in three dimensions relative to the tooth surfaces. In particular, these techniques do not take into account all five positional elements of a patient's teeth: rotation, height, angulation (or tip), torque, and in-out. Further, these existing techniques of indirect bonding provide minimal guidance as to how the actual position of a bracket compares to the clinician-defined prescription.

Therefore, a need exists for a physical bonding model and a method of indirect bonding that assist with optimal positional alignment of the brackets on the patient's teeth by taking into consideration all five positional elements of a patient's teeth. A need also exists for a method that even more so decreases chair time, decreases orthodontist time, lessens treatment time and lessens patient discomfort.

SUMMARY OF THE INVENTION

Orthodontic appliances such as orthodontic brackets or tubes typically include a retentive bonding pad or base, a body with a slot into which an archwire can be placed, and tie wings or ligating mechanisms to hold the archwire in place. According to one embodiment of the invention, a physical model is disclosed that comprises a three dimensional solid representation of one or more maloccluded teeth. The model further comprises a plurality of structures disposed on the facial surface of each model tooth for use in preferentially positioning an orthodontic appliance in three dimensions relative to the facial surface.

The positioning structures disclosed herein preferably include at least two ridge portions and from one to four pods. Each ridge portion preferably contacts and serves as a positioning guide for a different side portion of the bonding pad or base member of an orthodontic appliance, and two or more ridge portions can cooperate to preferentially position the appliance in the x- and y-dimensions relative to the facial surface of a model tooth. The pod or pods preferably contact the underside of an orthodontic appliance to preferentially position the base of the appliance in the z-dimension relative to the facial surface of a model tooth. The ridge portions and pods are preferably formed as a unitary part of a physical model that is made from a virtual model on which the preferred ridge and pod configurations for each tooth are determined. The ridges can, but need not, intersect, and the height of each pod can vary within practical limits determined by factors such as the base area of the orthodontic appliance, interference with adjacent model teeth due to inclination and spacing, and the like.

Once the positional relationship of the appliance base to the facial surface of the model tooth is determined in all three dimensions by means of the ridge portions and pod or pods, each appliance can be temporarily cemented to its respective model tooth using a releasable adhesive. Because the releasable adhesive will fill in the spaces around the pods beneath the base of the orthodontic appliance prior to curing, a solid, three dimensional bonding pad is formed beneath the base that will cause the appliance to reestablish the same positional alignment relative to the actual tooth from which the model was made when the appliance is removed from the model tooth and transferred to the actual tooth using indirect bonding techniques. The orthodontic appliance is thereby optimally positioned in a predetermined, desired positional relationship to the facial surface of the actual tooth for the application of therapeutic forces during treatment to achieve adjustments in rotation, height, angulation (or tip), torque, and in-out. This process can be accomplished quickly and effectively by using a transfer tray to lift and move the appliances from as many as 16 model teeth at once.

According to another preferred embodiment of the invention, an indirect bonding method is disclosed that begins by obtaining a direct impression or scanned image of the patient's teeth. The impression is converted into a digital image or a virtual model of the original malocclusion. Using any of several software applications, the teeth of the virtual model are manipulated to create the ideal corrected occlusion. Virtual brackets and tubes of various types as may be desired by the orthdontist are applied to the virtual model, and the software is then utilized to determine the optimum bracket position based on the final corrected occlusion.

According to one particularly preferred embodiment, the software then establishes the height and positioning of one vertical ridge and one horizontal ridge that serve as guides for the anterior-posterior or mesial-distal position (rotation) and the superior-inferior or occlusal/incisal-gingival position of the bracket base (height), or generally, the x and y axes. Since the contours of the tooth surface and the bracket base or pad are not necessarily congruent, the software then generates between one and four small, spaced-apart, pods of various heights, or other similarly effective spacers, for orienting the base of the orthodontic appliance relative to the surface of the virtual tooth in the "z" dimension. The "z" dimension can be referred to as "complex in and out" positioning of the bracket base, which affects torque, rotation, and actual in and out positioning of the brackets. The placement, position, and dimensions of the pods and ridges created by the computer software are based on the teeth in their corrected position as shown by the corrected virtual model. For purposes of this disclosure, the x, y, and z coordinate system discussed herein is preferably oriented so that, with regard to any particular tooth, the x-y plane lies in the facial surface of the tooth. The "x" direction is towards the mesial or distal surface of the tooth, the "y" direction is towards the gingival or incisal or occlusal surface of the tooth, and the "z" direction is away from the facial surface of the tooth.

The virtual corrected model with virtual brackets in place is then "re-wound" to the original malocclusion position. Any interferences with bracket placement in the maloccluded state is determined and accommodated. Ideal bracket placement may not be possible until further tooth movement has occurred. Likewise, the placement of aligning ridges and pods may require modification from the ideal, as discussed below.

Next, a physical model is created, preferably using a stereo lithographic process or other similarly effective method, with the appropriate ridges and pods on the surface of each tooth. The pods on the model control the spacing of the individual bracket bases or pads from the tooth and its angular relationship to the face of the tooth, and account for the torque and in-out positional elements (collectively "complex in-out") of the tooth. The ridges control the anterior-posterior (mesial-distal) and the superior-inferior (occlusal or incisal-gingival) positioning of the brackets and account for the height, rotation and angulation (or tip) positional elements of the tooth. In sum, the pods and ridges act cooperatively to precisely position the brackets in all three dimensions for maximum therapeutic benefit in moving the teeth to where they will eventually be in their corrected position.

After the physical model with the pods and ridges is created, adhesive that releasably mounts the brackets to the model is applied to the base of the brackets. Each bracket is placed in contact with the ridges on the tooth of the physical model to align the tooth in regard to height, rotation and angulation. The bracket is fully seated onto the pods. The adhesive enters the space between the tooth surface and the base of the bracket as it is supported by the pods to fill the void and form a dimensionally correct, custom-contoured bonding base.

The adhesive holding the brackets onto the model is then cured. The cured adhesive is permanently attached to the bracket pad or base but releasably attached to the physical model. A transfer tray is formed and molded over the brackets on the model. The transfer tray and model are then soaked in water to release the brackets from the model. After soaking, the transfer tray while gripping the brackets is removed from the model. A bonding agent is then applied to the brackets and the transfer tray transfers the brackets from the model to the patient's teeth. The transfer tray can transfer a plurality of brackets at once, or it can transfer one bracket at a time if the bracket needs to be replaced on a single tooth.

As a result of optimally positioning the bracket to take into consideration the five positional elements of a tooth, the arch-wire can be secured to the brackets with less custom bonding and fitting, and will apply forces to the teeth to move them more efficiently and effectively to the desired position. Use of the present invention reduces the need for adjusting the arch-wire and replacing or repositioning brackets, thereby also reducing orthodontist time, treatment time, chair time and patient discomfort.

BRIEF DESCRIPTION OF THE DRAWINGS

The apparatus of the invention is further described and explained in relation to the following figures of the drawings wherein:

FIG. 7 is an enlarged perspective view of a bracket with a mesh base;

FIG. 8a is an elevation view of a bracket releasably mounted on a tooth with a negative torque and showing pods supporting the bracket in a level position, partially spaced away from the tooth surface with respect to a z-axis;

FIG. 8b is an elevation view of a bracket releasably mounted on a tooth with a positive torque and showing pods supporting the bracket in a level position, partially spaced away from the tooth surface with respect to a z-axis;

FIG. 8c is an elevation view of a bracket releasably mounted on a tooth that is set-back and showing adhesive spacing the bracket away from the tooth surface;

FIG. 9 is a perspective view of a physical bonding model showing a material being molded over teeth and brackets to form a transfer tray;

Like reference numerals are used to describe like parts in all figures of the drawings.

DESCRIPTION OF THE PREFERRED EMBODIMENTS

Figure 1:
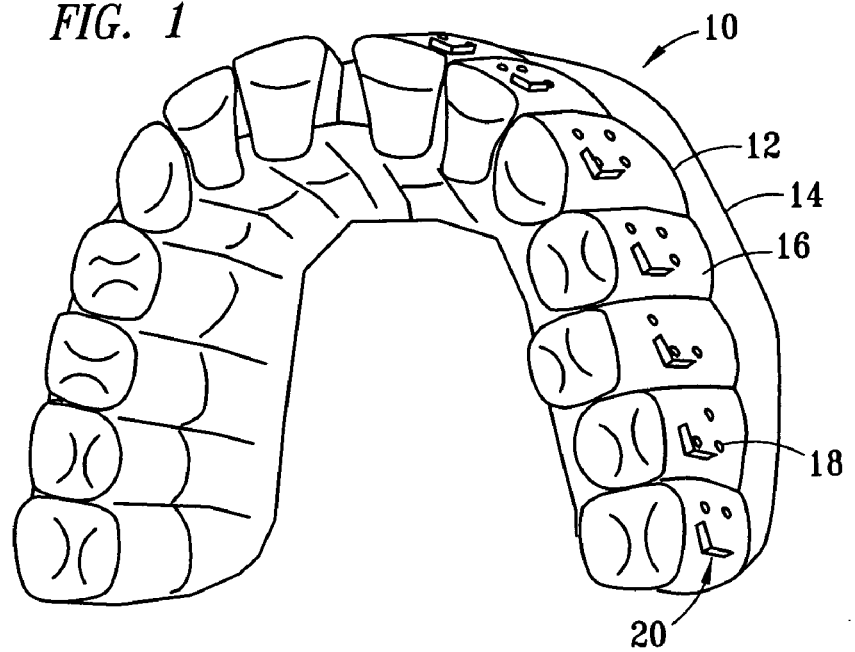
FIG. 1 is a perspective view of a physical bonding model of the invention with ridges and pods incorporated on a facial surface of teeth.

The method of the invention preferably begins with taking an impression of the patient's maloccluded teeth, which is used to form a plaster or stone tooth impression model. The impression model is then sent to a laboratory, scanned and converted into a digital file to form a virtual model. Although the use of an impression is a preferred method for creating a virtual model, other similarly effective alternative methods such as intra-oral scanning of the teeth can also be used. The original virtual malocclusion model is then manipulated using specialized computer software to reposition the teeth to their final or corrected state. This final or corrected state is used to create another virtual model, the corrected malocclusion model.

From the corrected malocclusion model, the ideal position of a virtual orthodontic appliance on the original malocclusion model can be determined. The virtual orthodontic appliance can be placed on a tooth of the original malocclusion model in an optimal location to account for all five positional elements of the tooth, which include height, rotation, angulation, torque and in-out, terms well known to orthodontists. This optimal appliance location can be used to apply forces to the tooth through an archwire and the appliances to move the maloccluded tooth to the position of the corresponding tooth in the corrected malocclusion model quickly and precisely. However, the ideal position of the orthodontic appliance as shown in the virtual model may not even be touching the facial surface of the tooth. In such cases, proper positioning of the appliance relative to the tooth requires some means for spacing the orthodontic appliance away from, or at a predetermined angle relative to, the tooth.

Based on this ideal position of the orthodontic appliance, at least one, and preferably one to four, virtual pods or bosses and at least two virtual ridge portions are created on the virtual original malocclusion model using computer software. Although the ridge portions and pods of the invention are explained in more detail below, the ridge portions act as guides to properly position the base of the appliance in the X- and Y-dimensions on the facial surface of the tooth, and to indicate where the appliance, such as a bracket, should be located relative to the facial surface of the tooth. The pods then preferably support the base of the appliance at the desired distance from the facial surface of the model tooth and in the proper orientation relative to the facial surface.

It should be noted that not every tooth in a virtual or physical malocclusion model will necessarily have ridges portions or pods. Some teeth may have only a partial ridge. A tooth may be so severely malposed that positioning the orthodontic appliance on the tooth would cause a collision or interference with the next tooth or bracket. In this case, the tooth will have to be moved incrementally and the bracket reset later. For this purpose, a second physical model with the teeth in the fully corrected positions should be produced. In some situations, a transfer tray can be created for a single tooth.

Once the ridge portions and pods are created on the virtual malocclusion model, a positive model embodying the same ridge portions and pods is manufactured from the virtual malocclusion model. One preferred apparatus suitable for use in fabricating a positive model from the virtual model is a stereo lithography apparatus (SLA). Simply stated, the SLA utilizes a controlled laser beam to selectively harden a thermosetting liquid resin into a physical structure corresponding to the virtual malocclusion model bearing the pods and ridges on the facial surface of the teeth. More detailed descriptions regarding SLA and other computer-aided fabrication techniques are publicly available, for example, in U.S. Pat. Nos. 6,699,037 and 6,688,885. Various commercially available materials can be used to create the positive malocclusion model, provided that the adhesive applied to the orthodontic appliance sticks but does not permanently adhere to the model.

It should also be understood that the method used to fabricate a physical model does not necessarily have to rely on computer manipulation of digital data. The present invention may, for example, be produced manually without using computer-aided techniques. For instance, the tooth impression model can be duplicated and one of the models can itself be manually manipulated to reposition the teeth into a corrected position. Based on this corrected position and the placement of the orthodontic appliances on the positive malocclusion model to efficiently and effectively achieve the corrected position, ridges can be formed on the malocclusion model to serve as guides for positioning the edge of the base of an orthodontic appliance relative to the facial surface of a tooth. Similarly, pods can be formed on the positive malocclusion model using plaster, for example, to fill in any voids between the facial surface of the tooth and the base of a correctly positioned orthodontic appliance. Although the present invention can be implemented using this manual method, the computer-aided techniques are preferred because they are more accurate and less time consuming.

Figure 2:
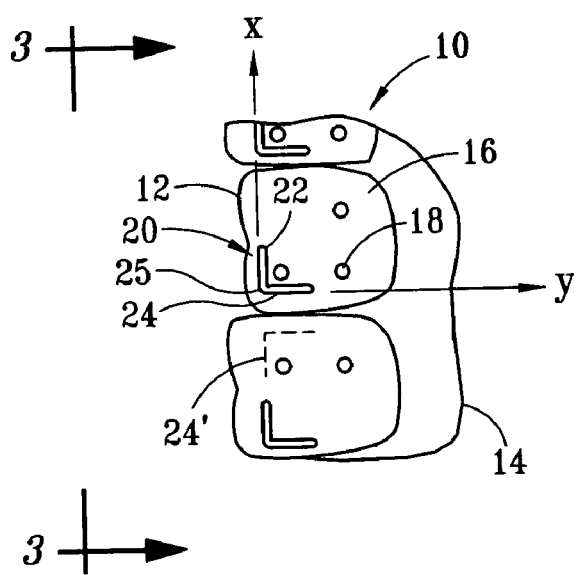
FIG. 2 is a detail view of a portion of the physical bonding model of FIG. 1.
Figure 3:
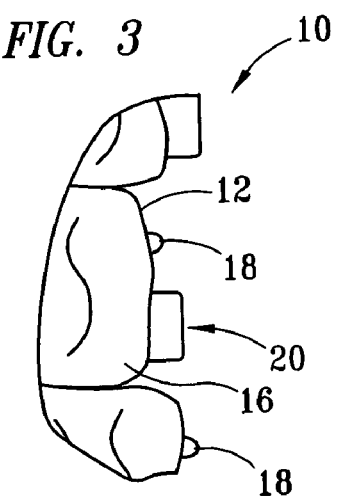
FIG. 3 is a side detail view taken along line 3-3 of FIG. 2.

Referring to FIG. 1, physical model (10) comprises teeth (12) implanted in gingival tissue (14). Facial surfaces (16) of teeth (12) include at least one pod (18) or boss and, preferably, at least two cooperating alignment ridge portions (20). FIGS. 2 and 3 show detail views of pods (18) and ridges (20).

Pods (18) are preferably dome-shaped to allow the orthodontic appliance to release more easily from pod (18). Pods (18) may need to be more tapered toward their gingival side so that as the orthodontic appliance is removed, the appliance can flex and slide over pod (18). The dimensions of individual pods (18) can vary as needed to obtain proper spatial alignment of the appliance relative to teeth (12) but preferably do not exceed about half a millimeter in height and diameter. The pod dimensions will typically need to be of a height and geometry that facilitates withdrawal of the orthodontic appliance.

The number, position, height and orientation of pods (18) on tooth (12) are preferably determined by the computer software based on the dimensions of the teeth and any interference between them. Although three pods can often stabilize an orthodontic appliance on a model tooth, the use of four pods per tooth will typically guarantee stability. In other cases, one or two pods may be all that is needed for optimal spatial positioning of the orthodontic appliance in relation to the facial surface of a tooth. The pods may, for example, be oriented diagonally or across from each other. While the use of from one to four pods is preferred, it should be understood that some model teeth may require no pods and the total number of pods per tooth is not limited to four.

Alignment ridges (20) preferably include horizontal ridge portion (22) along the x-axis and vertical ridge portion (24) along the y-axis of model (10). "X" ridge portion (22) and "y" ridge portion (24) preferably intersect to form a right angle or corner (25), although it is not required that the cooperating ridge portions intersect or abut each other, or that they be at right angles to each other, so long as their combined effect is to properly position an orthodontic appliance in the x-y plane on the facial surface of a model tooth.

"X" ridge portion (22) is preferably placed on the occlusal or incisal surface of tooth (12) to allow for trimming of the orthodontic appliance on its gingival margin, as the appliance is almost never trimmed on its occlusal or incisal margins. The "y" ridge portion is preferably placed on either the mesial surface or distal surface depending on the rotation of tooth (12) and access with the orthodontic appliance. "Y" ridge portion (24) is shown in solid outline on the distal surface and "y" ridge portion (24') is shown in dashed outline on the mesial surface. One of the vertical margins of the orthodontic appliance may need to be trimmed to clear an adjacent tooth, so "y" ridge portion (24) is preferably placed on the untrimmed side. However, it should be understood that in rare cases, neither the mesial surface nor the distal surface is accessible for an untrimmed orthodontic appliance. In these cases, another physical malocclusion model with the alignment ridges and pods can be created from the virtual model depicting the partially corrected tooth position after real tooth movement produces sufficient clearance to allow access. The height, length and width of alignment ridges can vary within the scope of the invention and will most preferably be of a height and geometry that facilitates the placement of a corner of an orthodontic appliance against the ridge. For example, the "x" ridge and "y" ridge portions on one tooth may not have the same dimensions based on the extent the bracket is spaced from the facial surface of the tooth.

Once the physical model (10) bearing the ridge portions and pods as described above is formed, the orthodontic appliances can be placed on the model teeth (12). As previously mentioned, the orthodontic appliances are preferably brackets or buccal tubes. Referring to FIG. 7, bracket (26) of the invention is a commercially available orthodontic appliance that is bonded to the patient's tooth for the purpose of fastening an archwire. Bracket (26) is preferably fabricated from metal, ceramic, or plastic, or a combination of any of the three materials. Bracket (26) shown in FIG. 7 is designed to bond to incisors or bicuspids and includes a body (28) which has a slot (30) to receive the archwire. The underside of body (28) of bracket (26) is attached to a pad (32) and the underside of pad (32) is attached to a mesh base (34). In contrast to the bracket shown in FIG. 7, orthodontic appliances used with molars commonly have tubes where the end of the archwire is received. These appliances are often referred to as "buccal tubes." However, it should be understood that the method of the invention can be utilized with brackets that attach to incisors or bicuspids, buccal tubes that attach to the molars, or any other device that can be mounted onto a patient's tooth to receive an archwire or head gear. Throughout the disclosure, brackets and buccals tube are used as examples of orthodontic appliances that can be efficiently and effectively positioned through use of the present invention.

Figure 4:
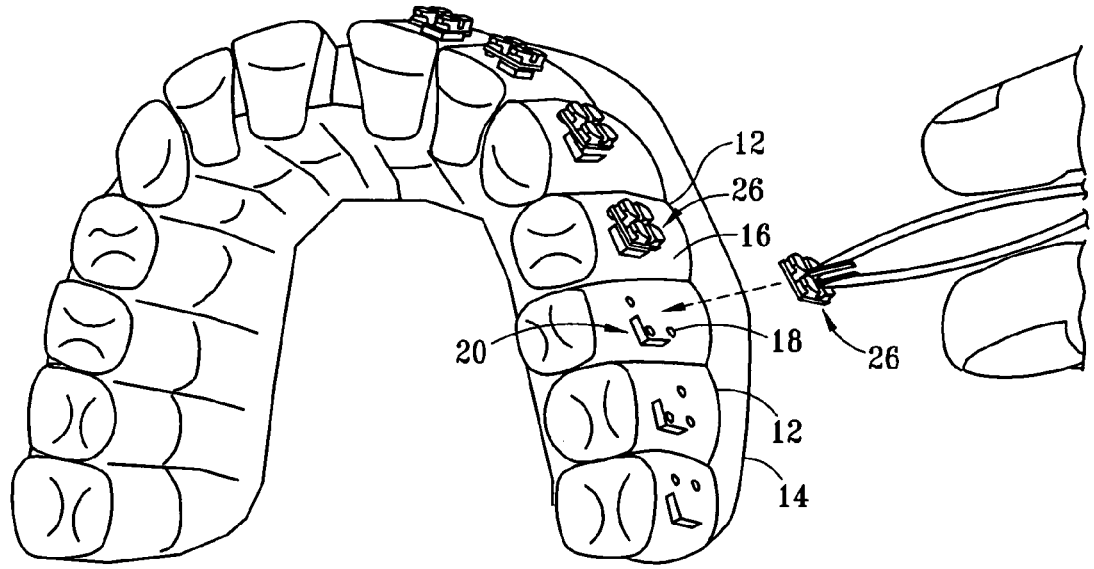
FIG. 4 is a perspective view of a physical bonding model of the invention showing brackets in contact with ridges and pods on a facial surface of teeth.
Figure 5:
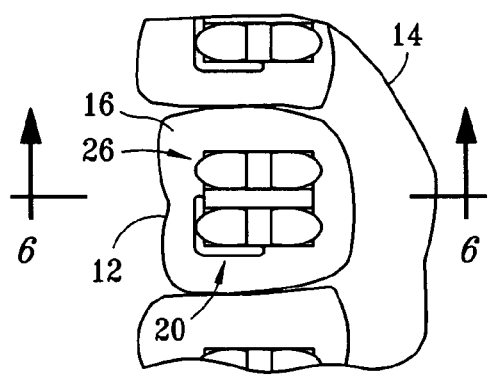
FIG. 5 is a detail view of a portion of the physical bonding model of FIG. 4.
Figure 6A:
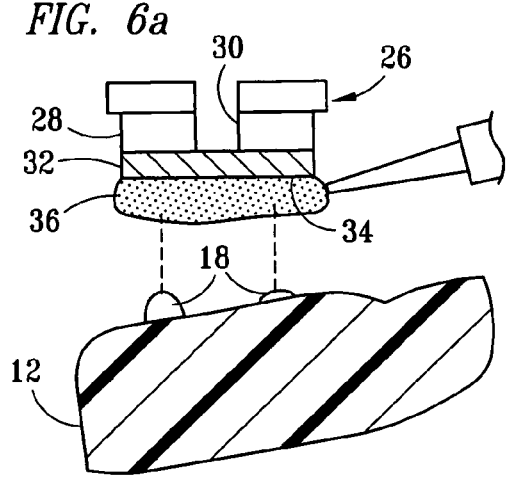
FIG. 6a is an exploded cross-sectional view taken along line 6-6 of FIG. 5 and illustrates adhesive applied to the underside of a bracket that will surround pods.

FIG. 4 illustrates a plurality of brackets (26) mounted on facial surface (16) of teeth (12) and a bracket (26) about to be placed on facial surface (16) of model tooth (12). FIG. 5 shows a detailed view of the plurality of mounted brackets (26) of FIG. 4. To mount brackets (26), liquid adhesive (36) is applied to mesh base (34), as shown in FIG. 6A. Adhesive (36) is preferably selected from various commercially available adhesive materials that will attach more securely, for example, to the mesh bonding pad typically found on the underside of the base of brackets (26) than to the relatively slicker surface of model (10). Properly positioned and aligned brackets (26) should be releasable from model (10) even after the adhesive sets sufficiently to form a solid bonding pad capable of supporting bracket (26) in a preferred positional and spatial alignment relative to model tooth (12).

Figure 6B:
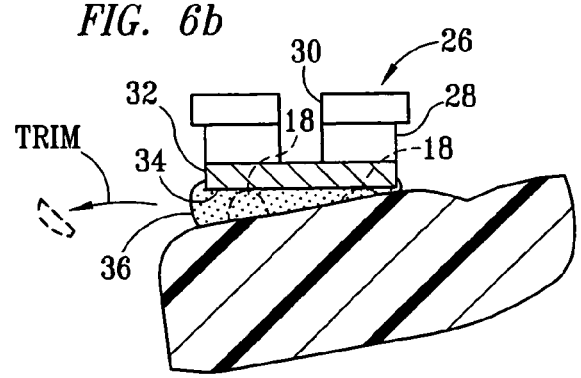
FIG. 6b is a view as in FIG. 6a but showing a bracket releasably mounted on a model with adhesive surrounding pods.

Bracket (26) with adhesive (36) is desirably placed on tooth (12) of model (10) with slot (30) oriented relative to facial surface (16) of tooth (12) so that an archwire can be attached to a plurality of brackets. Bracket (26) is placed with one corner of pad (32) of bracket (26) contacting corner (25) of ridge (20), and with mesh base (34) of bracket (26) contacting pods (18). The contact between pods (18) and mesh base (34) is shown in FIG. 6b, where it is also shown that any surplus adhesive (36) is removed after positioning the bracket on the model.

The contact between mesh base (34) and pods (18) allows the adhesive on mesh base (34) around pods (18) to create a thickness of layer based on the height of the pod. The higher the pod, the thicker the adhesive. This thickness spaced bracket (26) away from tooth (12) along the z-axis (which is labeled in FIGS. 8a, 8b and 8c) and accounts for the complex in-out dimension of tooth (12) to optimally position bracket (26) on tooth (12).

Multiple pods (18) associated with a single tooth (12) can have varying heights, which in turn means that adhesive (36) adhering to bracket (26) placed on tooth (12) can have varying thickness. FIGS. 8a and 8b show examples of this variation. FIG. 8a illustrates that pod (18) near occlusal surface or incisal surface (38) is taller than pod (18) near gingival surface (40). Altering the pod heights, thereby altering the bracket postion in the z-dimension, will alter the torque properties for any given bracket placement in the x- and y-dimensions. For example, adhesive (36) is thicker near occlusal surface or incisal surface (38) than it is near gingival surface (40). This thickness near occlusal surface or incisal surface (38) accounts for the excess negative torque or the crown of tooth (12) tipping in. Because of the negative torque, bracket (26) has been raised by adhesive (36) at an angle ($\theta$) in the z-axis direction.

In contrast, in FIG. 8b, pod (18) near gingival surface (40) is taller than pod (18) near occlusal surface or incisal surface (38) and, therefore, adhesive (36) is thicker near gingival surface (40) than near occlusal surface or incisal surface (38). This thickness near gingival surface (40) accounts for the excess positive torque or the crown of tooth (12) tipping out. Because of the positive torque, bracket (26) has been raised by adhesive (36) at an angle ($\theta$) in the z-axis direction.

Pods (18) may also be the same height, as shown in FIG. 8c, if tooth (12) does not have much inclination or rotation, or if tooth (12) is near its corrected or final position. In this case, bracket (26) has been raised straight up in the z-axis direction so that slot (30) will line up evenly with other slots so that an archwire mounted to brackets (26) is essentially straight. As mentioned previously, pods (18) control the complex in-out positional element of a tooth by controlling the spacing of an individual bracket away from the tooth and by controlling the bracket's angular relationship to facial surface of the tooth (16).

As best illustrated in FIG. 5, one corner of bracket (26) is in contact with corner (25) of ridge (20). This contact permits the side walls of pad (32) to align with the inside walls of "x" ridge portion (22) and "y" ridge portion (24) in order to align bracket (26) on tooth (12). The placement of bracket (26) in contact with "x" ridge portion (22) and "y" ridge portion (24) allows for the precise height, rotation and angulation placement of bracket (26) onto tooth (12) of model (10). In other words, the alignment ridges (20) set the bracket from front-to-back and top-to-bottom of tooth (12). If, for example, bracket (26) is placed too far back on facial surface (16) of tooth (12), incorrect rotational movement may occur. After the placement of brackets (26) on teeth (12), adhesive (36) is then cured, preferably using chemical or light activation.

Referring to FIG. 9, an indirect bonding tray or transfer tray (42) is formed over and in contact with brackets (26), and is used to transfer brackets (26) on model (10) to the patient's mouth. While an indirect bonding tray or transfer tray is disclosed herein to transfer the brackets from the model to the patient's teeth, one skilled in the art would understand that other systems or means could be used for transfer. Transfer tray (42) can also contain individual brackets for transfer. For purposes of this invention, transfer tray (42) should be semi-rigid and eventually allow the release of the orthodontic appliance. Preferably, transfer tray (42) is made with a silicone transfer material mixed with an activating agent. Once the material and agent have been mixed, the mixture is rolled into the shape of a cylinder and molded over brackets (26). The occlusal and lingual surfaces of the teeth are preferably covered with the tray mixture.

There are many ways to form transfer tray (42) and U.S. Pat. No. 6,554,613, for example, gives a general discussion of a few such ways. It should be understood that the process by which transfer tray (42) is formed is not limited to the description in this application. For example, a Biostar unit can be used to form transfer tray (42). The Biostar unit pressure forms a layer of soft material, over layered with a more rigid material. The layer of soft material is pressure formed onto model (10) first, and the excess material is trimmed off. The layer of more rigid material is then adapted and then trimmed away, since it is only to permit firm seating of the soft tray. The outer layer provides rigidity to the transfer tray, and the inner layer permits easier removal of the tray.

In addition, polyvinylsiloxane, or PVS, can be used to form transfer tray (42). To form tray (42), two phases of PVS are used: a light body material and a heavy body material. The light body material is squirted using a syringe around set brackets (26) on model (10). The light body material flows into all the contours of brackets (26) and forms a grip on them. The heavy body material is then applied over the light body material to form a support tray.

Figure 10:
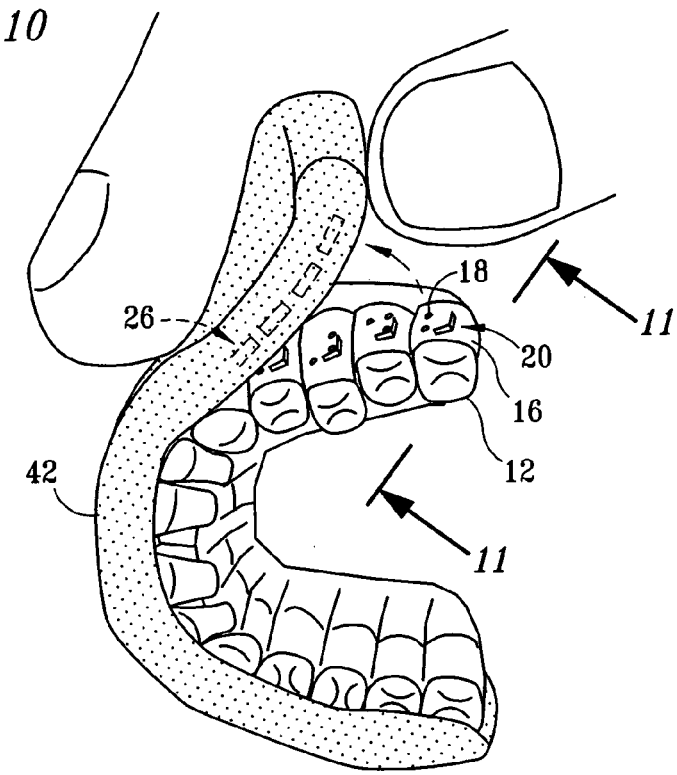
FIG. 10 is a perspective view of a physical bonding model showing brackets being lifted from a model and held in a transfer tray.
Figure 11:
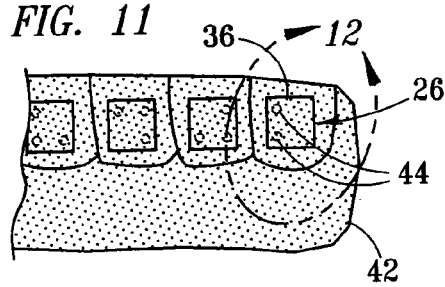
FIG. 11 is a fragmentary view taken along line 11-11 of FIG. 10 showing a portion of the transfer tray with brackets held inside.
Figure 12:
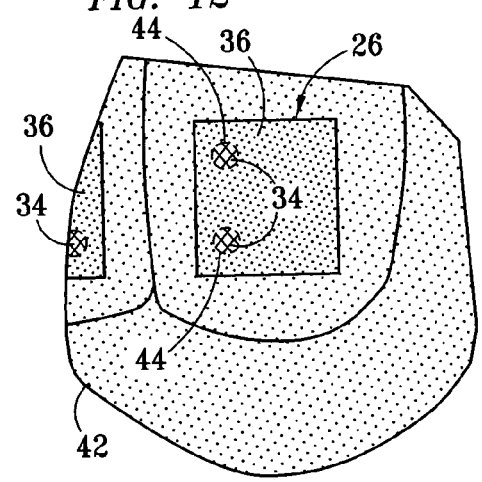
FIG. 12 is a detail view taken from FIG. 11 showing an underside of a bracket having adhesive thereon and showing indentations in the adhesive left by pods.

To remove brackets (26) from model (10), model (10) with transfer tray (42) is preferably soaked in water for a sufficient time to permit the separation of adhesive (36) from tooth (12). Referring to FIG. 10, as transfer tray (42) is removed from model (10), brackets (26) remain stuck to the inside of transfer tray (42) and pods (18) and ridges (20) on model (10) are left behind. FIG. 11 shows the inside of tray (42) with brackets (26) stuck and adhesive (36) exposed. Indentations (44) from pods (18) are shown in adhesive (36). A closer look at indentations (44) in FIG. 12 shows mesh base (34) at the bottom of indentations (44). Mesh base (34) can be seen as a result the contact between pods (18) and mesh base (34). Although pods (18) were in contact with mesh base (34), mesh base (34) may still have a very small layer of adhesive (36) covering it because of the surface area in the mesh.

Figure 13:
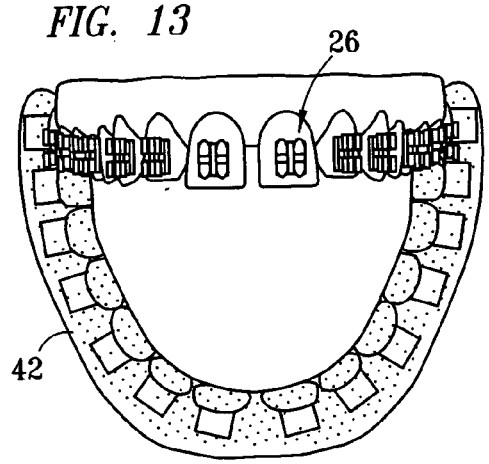
FIG. 13. is a front view of brackets bonded to a patient's teeth with a transfer tray removed.

The surface of adhesive (36) is then carefully cleaned using micro-etching or sandblasting. This ensures that a receptive surface is present in terms of receiving a clinical bonding agent. Any excess material on tray (42) is also trimmed. After cleaning and trimming, conventional indirect bonding techniques are used to bond brackets (26) to the patient's teeth. A bonding agent is applied to brackets (26) and transfer tray (42) is used to transport brackets (26) to the patient's teeth, as shown in FIG. 13. When transfer tray (42) is applied to the patient's mouth, brackets (26) are removed from tray (42) in the proper positional relationship for application to the patient's teeth. In other words, brackets (26) are bonded to the patient's teeth in the same optimal position as they were placed on model (10) and adhesive (36) maintains the same spacing.

Other alternations and modifications of the invention will likewise become apparent to those of ordinary skill in the art upon reading the present disclosure, and it is intended that the scope of the invention disclosed herein be limited only by the broadest interpretation of the appended claims to which the inventor is legally entitled.

The invention claimed is:

1. A method for indirectly positioning and bonding an orthodontic appliance on a maloccluded tooth, the method comprising the steps of:
   forming a physical model corresponding to teeth of a patient, the model having a plurality of model teeth with each tooth having a facial surface, and each maloccluded model tooth embodying at least one protuberance that is a unitary part of the facial surface and at least two non-parallel cooperating ridges that are unitary parts of the facial surface;
   obtaining at least one orthodontic appliance and applying adhesive to a base of the at least one orthodontic appliance;
   positioning an orthodontic appliance over the at least one protuberance and adjacent to the at least two ridges of a maloccluded model tooth;
   using the at least two ridges to guide the placement of the orthodontic appliance on the facial surface of a maloccluded model tooth;
   releasably mounting the at least one orthodontic appliance to the physical model on top of the at least one protuberance and in contact with walls of the at least two cooperating ridges;
   applying an adhesive to the base of an orthodontic appliance, wherein the adhesive is at least as thick as the height of the at least one protuberance and at least at the position of the at least one protuberance on the facial surface;
   forming an adhesive layer on the base of the at least one orthodontic appliance by allowing the adhesive to spread and shape between the at least one tooth of the model and the base;
   curing the adhesive layer;
   forming a transfer tray over the at least one tooth and the at least one orthodontic appliance;
   removing the transfer tray and the at least one orthodontic appliance from the model; and
   transferring and bonding the at least one orthodontic appliance to the maloccluded teeth of the patient.

2. The method of claim 1 further comprising the step of soaking the transfer tray and model in a liquid to aid in releasing the adhesive from the model.

3. The method of claim 1 further comprising the step of cleaning the adhesive after removal of the at least one orthodontic appliance from the model.

4. The method of claim 1 wherein the physical model is formed by stereo lithography.

5. The method of claim 1 wherein the physical model is formed by molding.

6. The method of claim 1 wherein the physical model is formed by carving.

7. The method of claim 1 wherein the model is formed from a polymeric material.

8. The method of claim 1 wherein the at least one protuberance has a maximum height of about half a millimeter.

9. The method of claim 1 wherein each maloccluded model tooth embodies from one to four protuberances.

10. The method of claim 1 wherein at least one maloccluded model tooth embodies at least two protuberances of different heights.

11. The method of claim 1 wherein at least one maloccluded model tooth embodies two protuberances that are unitary parts of the facial surface.

12. The method of claim 1 wherein at least one maloccluded model tooth embodies three protuberances that are unitary parts of the facial surface.

13. The method of claim 1 wherein at least one maloccluded model tooth embodies four protuberances that are unitary parts of the facial surface.

14. The method of claim 1 wherein a plurality of orthodontic appliances are transferred and bonded to a patient's maloccluded teeth.

15. A method of forming a physical model to aid in positioning orthodontic appliances on a patient's teeth according to a position obtained from a virtual model, the method comprising the steps of:

creating a virtual original malocclusion model of a patient's teeth, including the facial surfaces thereof;

manipulating the virtual original malocclusion model to simulate movement of individual teeth to a corrected position;

creating a virtual corrected malocclusion model from the manipulated virtual original malocclusion model based on the final corrected teeth positions;

positioning a virtual orthodontic appliance on the virtual original malocclusion model according to the corrected positions obtained from the virtual corrected malocclusion model;

modifying at least one virtual original malocclusion model tooth to embody at least one virtual protuberance that is a unitary part of the facial surface where the size, position, and orientation of the at least one virtual protuberance correspond to the spacing, positioning, and orientation of the virtual orthodontic appliance on the virtual original malocclusion model;

modifying at least one virtual original malocclusion model tooth to embody at least two non-parallel cooperating virtual ridges that are unitary parts of the facial surface, where the size, position, and orientation of the at least two cooperating virtual ridges correspond to the spacing, positioning, and orientation of the virtual orthodontic appliance on the virtual original malocclusion model; and forming a physical model of the modified virtual original malocclusion model with at least one physical maloccluded model tooth embodying at least one protuberance and at least two cooperating non-parallel ridges that are unitary parts of the facial surface, wherein the size, position, and orientation of the at least one protuberance and the at least two ridges embodied on the physical model tooth correspond to the size, position, and orientation of the at least one virtual protuberance and the at least two cooperating virtual ridges on the facial surface of the at least one modified virtual original malocclusion model tooth.

* * * * *